(12) United States Patent
Davies et al.

(10) Patent No.: US 11,937,873 B2
(45) Date of Patent: Mar. 26, 2024

(54) ELECTROSURGICAL DEVICE HAVING A LUMEN

(71) Applicant: Boston Scientific Medical Device Limited, Ballybrit (IE)

(72) Inventors: Gareth Davies, Toronto (CA); John Paul Urbanski, Toronto (CA); Rund Abou-Marie, Mississauga (CA)

(73) Assignee: Boston Scientific Medical Device Limited, Ballybrit (IE)

( * ) Notice: Subject to any disclaimer, the term of this patent is extended or adjusted under 35 U.S.C. 154(b) by 917 days.

(21) Appl. No.: 16/935,533

(22) Filed: Jul. 22, 2020

(65) Prior Publication Data
US 2021/0000536 A1 Jan. 7, 2021

Related U.S. Application Data

(63) Continuation-in-part of application No. 14/851,353, filed on Sep. 11, 2015, now Pat. No. 10,765,473,
(Continued)

(51) Int. Cl.
*A61B 18/14* (2006.01)
*A61B 18/00* (2006.01)

(52) U.S. Cl.
CPC .............. *A61B 18/1492* (2013.01); *A61B 2018/00077* (2013.01); *A61B 2018/00083* (2013.01);
(Continued)

(58) Field of Classification Search
CPC ...... A61B 18/1492; A61B 2018/00029; A61B 2018/00101; A61B 2018/00357;
(Continued)

(56) References Cited

U.S. PATENT DOCUMENTS 175,254 A 3/1876 Oberly
827,626 A 7/1906 Gillet
(Continued)

FOREIGN PATENT DOCUMENTS

DE 0257754 11/1911
DE 2822829 A1 11/1979
(Continued)

OTHER PUBLICATIONS

European Search Report for European Application No. 14764721.8 dated Sep. 16, 2016.
(Continued)

*Primary Examiner* — Tigist S Demie
(74) *Attorney, Agent, or Firm* — Nelson Mullins Riley & Scarborough LLP

(57) ABSTRACT

An electrosurgical device comprises an electrically conductive elongate member for traversing body vasculature defining a hollow lumen with one or more apertures at or near its distal end, wherein electrical energy can flow through the wall of the elongate member; and an energy delivery device in electrical communication with the elongate member is located distal to the end of the elongate member. The energy delivery device includes an electrode for delivering energy. Methods of using the electrosurgical device include cutting through occlusions and creating transseptal punctures.

6 Claims, 14 Drawing Sheets

Related U.S. Application Data which is a continuation-in-part of application No. PCT/IB2014/059830, filed on Mar. 14, 2014, and a continuation-in-part of application No. PCT/IB2014/059696, filed on Mar. 12, 2014.

(60) Provisional application No. 61/781,231, filed on Mar. 14, 2013, provisional application No. 61/777,368, filed on Mar. 12, 2013.

(52) U.S. Cl.
CPC ............... *A61B 2018/0022* (2013.01); *A61B 2018/00351* (2013.01); *A61B 2018/00773* (2013.01); *A61B 2218/001* (2013.01); *A61B 2562/0247* (2013.01)

(58) Field of Classification Search
CPC .. A61B 2018/0041; A61B 2018/00601; A61B 2018/1472; A61B 2218/002
See application file for complete search history.

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,587,972 A | 5/1986 | Morantte, Jr. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,246,438 A | 9/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,330,520 A | 7/1994 | Maddison et al. |
| 5,364,393 A | 11/1994 | Auth et al. |
| 5,372,596 A | 12/1994 | Klicek et al. |
| 5,380,304 A | 1/1995 | Parker |
| 5,383,876 A | 1/1995 | Nardella |
| 5,397,304 A | 3/1995 | Truckai |
| 5,398,683 A | 3/1995 | Edwards et al. |
| 5,403,338 A | 4/1995 | Milo |
| 5,423,809 A | 6/1995 | Klicek |
| 5,425,382 A | 6/1995 | Golden et al. |
| 5,449,370 A | 9/1995 | Vaitekunas |
| 5,462,521 A | 10/1995 | Brucker et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,643,197 A | 7/1997 | Brucker et al. |
| 5,643,255 A | 7/1997 | Organ |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,718,701 A | 2/1998 | Shai et al. |
| 5,720,744 A | 2/1998 | Eggleston et al. |
| 5,741,249 A | 4/1998 | Moss et al. |
| 5,743,905 A | 4/1998 | Eder et al. |
| 5,766,135 A | 6/1998 | Terwilliger |
| 5,779,688 A | 7/1998 | Imran et al. |
| 5,782,900 A | 7/1998 | De et al. |
| 5,810,764 A | 9/1998 | Eggers et al. |
| 5,814,028 A | 9/1998 | Swartz et al. |
| 5,824,026 A | 10/1998 | Diaz |
| 5,830,214 A | 11/1998 | Flom et al. |
| 5,836,875 A | 11/1998 | Webster, Jr. |
| 5,836,946 A | 11/1998 | Diaz et al. |
| 5,848,986 A | 12/1998 | Lundquist et al. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,913,854 A | 6/1999 | Maguire et al. |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,471 A | 9/1999 | De et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 5,992,418 A | 11/1999 | De et al. |
| 6,001,095 A | 12/1999 | De et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,172 A | 4/2000 | Hovda et al. |
| 6,053,870 A | 4/2000 | Fulton, III |

(56) References Cited

U.S. PATENT DOCUMENTS

| | | |
|---|---|---|
| 6,053,904 A | 4/2000 | Scribner et al. |
| 6,056,747 A | 5/2000 | Saadat et al. |
| 6,063,077 A | 5/2000 | Schaer |
| 6,063,093 A | 5/2000 | Winston et al. |
| 6,080,151 A | 6/2000 | Swartz et al. |
| 6,093,185 A | 7/2000 | Ellis et al. |
| 6,099,524 A | 8/2000 | Lipson et al. |
| 6,106,515 A | 8/2000 | Winston et al. |
| 6,106,520 A | 8/2000 | Laufer et al. |
| 6,117,131 A | 9/2000 | Taylor |
| 6,120,499 A | 9/2000 | Dickens et al. |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,192,280 B1 | 2/2001 | Sommer et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,234,178 B1 | 5/2001 | Goble et al. |
| 6,241,666 B1 | 6/2001 | Pomeranz et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,405,067 B1 | 6/2002 | Mest et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,477,396 B1 | 11/2002 | Mest et al. |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,638,222 B2 | 10/2003 | Chandrasekaran et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,775 B2 | 3/2004 | Devore |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,767,338 B2 | 7/2004 | Hawk et al. |
| 6,811,544 B2 | 11/2004 | Schaer |
| 6,814,733 B2 | 11/2004 | Schwartz et al. |
| 6,820,614 B2 | 11/2004 | Bonutti |
| 6,823,218 B2 | 11/2004 | Berube |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,027,873 B2 | 4/2006 | Pajunk et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,593,778 B2 | 9/2009 | Chandran et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,706,894 B2 | 4/2010 | Stewart et al. |
| 7,828,796 B2 | 11/2010 | Wong et al. |
| 7,900,928 B2 | 3/2011 | Held et al. |
| 8,192,425 B2 | 6/2012 | Mirza et al. |
| 8,241,313 B2 | 8/2012 | McFarlin et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0111620 A1 | 8/2002 | Cooper et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0069522 A1 | 4/2003 | Jacobsen et al. |
| 2003/0130655 A1 | 7/2003 | Woloszko et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0181855 A1 | 9/2003 | Simpson et al. |
| 2003/0225392 A1 | 12/2003 | McMichael et al. |
| 2004/0015162 A1 | 1/2004 | McGaffigan |
| 2004/0019350 A1 | 1/2004 | O'Brien et al. |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Molante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181138 A1 | 9/2004 | Hindricks et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0043728 A1* | 2/2005 | Ciarrocca .......... A61B 18/1482 606/50 |

(56) References Cited

U.S. PATENT DOCUMENTS

| | | |
|---|---|---|
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0090816 A1 | 4/2005 | McClurken et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0235381 A1 | 10/2006 | Whayne et al. |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0043349 A1 | 2/2007 | Swanson et al. |
| 2007/0060879 A1 | 3/2007 | Weitzner et al. |
| 2007/0066878 A1 | 3/2007 | Worley et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2008/0287944 A1 | 11/2008 | Pearson et al. |
| 2008/0294158 A1 | 11/2008 | Pappone et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0240237 A1 | 9/2009 | Goldfarb et al. |
| 2009/0264977 A1 | 10/2009 | Bruszewski et al. |
| 2010/0069734 A1 | 3/2010 | Worley et al. |
| 2010/0070050 A1 | 3/2010 | Mathis et al. |
| 2010/0087789 A1 | 4/2010 | Leeflang et al. |
| 2010/0114017 A1 | 5/2010 | Lenker et al. |
| 2010/0125282 A1 | 5/2010 | Machek et al. |
| 2010/0137859 A1 | 6/2010 | Wang |
| 2010/0168684 A1 | 7/2010 | Ryan |
| 2010/0168739 A1 | 7/2010 | Wu et al. |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2010/0204691 A1 | 8/2010 | Bencini |
| 2010/0211076 A1 | 8/2010 | Germain et al. |
| 2011/0046619 A1 | 2/2011 | Ducharme |
| 2011/0118582 A1 | 5/2011 | De La Rama et al. |
| 2011/0118735 A1 | 5/2011 | Abou-Marie et al. |
| 2011/0130648 A1 | 6/2011 | Beeckler et al. |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0029444 A1 | 2/2012 | Anderson |
| 2012/0143293 A1 | 6/2012 | Mauch et al. |
| 2012/0172857 A1 | 7/2012 | Harrison et al. |
| 2012/0232546 A1 | 9/2012 | Mirza et al. |
| 2012/0265055 A1 | 10/2012 | Melsheimer et al. |
| 2012/0277730 A1 | 11/2012 | Salahieh et al. |
| 2012/0330121 A1 | 12/2012 | Anderson et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0100561 A1 | 4/2014 | Biadillah et al. |
| 2014/0206987 A1 | 7/2014 | Urbanski et al. |
| 2014/0296769 A1 | 10/2014 | Hyde et al. |
| 2015/0231367 A1 | 8/2015 | Salstrom et al. |
| 2016/0220741 A1 | 8/2016 | Garrison et al. |
| 2017/0232234 A1 | 8/2017 | McDaniel et al. |
| 2019/0021763 A1 | 1/2019 | Zhou et al. |
| 2019/0247035 A1 | 8/2019 | Gittard et al. |
| 2022/0354572 A1 | 11/2022 | Davies et al. |

FOREIGN PATENT DOCUMENTS

| | | |
|---|---|---|
| EP | 0667126 A1 | 8/1995 |
| EP | 1169976 A1 | 1/2002 |
| EP | 2204134 A1 | 7/2010 |
| EP | 2968846 A1 | 1/2016 |
| JP | H03-53255 U | 5/1991 |
| JP | 11-089937 A | 4/1999 |
| JP | 2004-275765 A | 10/2004 |
| JP | 2005-521465 A | 7/2005 |
| JP | 2011-115581 A | 6/2011 |
| JP | 2012-510831 A | 5/2012 |
| WO | 99/62414 A1 | 12/1999 |
| WO | 03/82134 A1 | 10/2003 |
| WO | 2007/090075 A2 | 8/2007 |
| WO | 2012/061161 A1 | 5/2012 |
| WO | 2012/088601 A1 | 7/2012 |

OTHER PUBLICATIONS

European Supplementary Search Report for Application No. EP 14763003 completed on Sep. 9, 2016.

International Search Report and Written Opinion received for PCT Patent Application No. PCT/IB2014/059696, dated May 7, 2014, 22 pages.

International Search Report and Written Opinion received for PCT Patent Application No. PCT/IB2014/059830, dated Aug. 27, 2014, 14 pages.

Japanese Office Action for corresponding Application No. JP2015-562534 dated Dec. 26, 2017.

Japanese Office Action for counterpart Japanese Application No. 2015-562497, dated Dec. 26, 2017.

JP Office Action dated Aug. 14, 2018.

Patent Cooperation Treaty, International Preliminary Report on Patentability, International Application No. PCT/IB2014/059641, dated Sep. 15, 2015.

Translation of abstract of JPH03-53255U.

Office Action for corresponding Japanese application No. 2021-016433, dated Dec. 23, 2021.

Translation of Office Action for corresponding Japanese application No. 2021-016433, dated Dec. 23, 2021.

* cited by examiner

ELECTROSURGICAL DEVICE HAVING A LUMEN

CROSS-REFERENCES TO RELATED APPLICATIONS

This application is a continuation-in-part of international application PCT/IB2014/059830, filed Mar. 14, 2014, which claims the benefit of U.S. provisional application 61/781,231, filed Mar. 14, 2013 and a continuation-in-part of international application PCT/IB2014/059696, filed Mar. 12, 2014, which claims the benefit of U.S. provisional application 61/781,231, filed Mar. 14, 2013 and U.S. provisional application "Medical Device Having a Support Wire", No. 61/777,368, filed 12 Mar. 2013. All of the aforementioned applications are hereby incorporated by reference in their entirety. This application incorporates by reference, in their entirety, the contents of U.S. application Ser. No. 12/926,292, filed Nov. 8, 2010, and titled "Electrosurgical device for creating a channel through a region of tissue and methods of use thereof", and U.S. patent application Ser. No. 13/286,041, filed on Oct. 31, 2011, and U.S. Pat. No. 8,048,071, issued Nov. 1, 2011.

TECHNICAL FIELD

The disclosure relates to an electrosurgical device. More specifically, it relates to an electrosurgical device for applying electrical energy to cut through tissue in a region of a patient's body.

SUMMARY OF THE DISCLOSURE

An electrosurgical device operable to traverse body vasculature to deliver a fluid and electrical energy about its distal end is disclosed herein. The electrosurgical device comprises an electrically conductive elongate member for traversing body vasculature wherein electrical energy is deliverable through the wall of the elongate member; a lumen defined by the elongate member; one or more distal apertures defined at or near the distal end of the elongate member and in fluid communication with the lumen; and an energy delivery device in electrical communication with the elongate member at or about the distal end of the elongate member. The energy delivery device includes an electrode for delivering energy. A thermal shield (also referred to herein as a spacer) is positioned between the electrode and the elongate member for thermally protecting portions of the electrosurgical device.

In a first broad aspect, embodiments of the present invention include an electrosurgical device comprising an elongate member with an electrically conductive wall for delivering electrical energy therethrough, the elongate member defining a lumen that is in fluid communication with at least one distal aperture; an energy delivery device including an electrode electrically coupled to the wall of the elongate member; and an electrically insulative thermal shield between the electrode and the elongate member. In some embodiments, the electrode is at the distal tip of the electrosurgical device.

As a feature of the first broad aspect, in some embodiments the electrosurgical device further comprises a layer of insulation covering the elongate member, and the electrically insulative thermal shield is located between the layer of insulation and the electrode in order to protect the layer of insulation from heat generated by delivery of energy via the electrode. In some embodiments, a distal portion of the layer of insulation overlaps both the distal end of the elongate member and a proximal portion of the thermal shield.

As another feature of the first broad aspect, certain embodiments include a flexible elongate member.

As another feature of the first broad aspect, in some embodiments of the electrosurgical device, the proximal end of the energy delivery device further comprises an energy delivery device coupler for electrically coupling with the elongate member. In some embodiments, the energy delivery device has an intermediate portion for accommodating the thermal shield. Some such embodiments include the energy delivery device coupler comprising an electrically conductive spacer fitting within and substantially blocking a distal part (including the distal end) of the lumen, with the electrically conductive spacer in electrical communication with an electrically conductive surface of the wall of the elongate member. The energy delivery device can further comprise an intermediate conductive element extending between the electrically conductive spacer and the electrode, and, in some such embodiments, the thermal shield surrounds the intermediate conductive element. In some embodiments the thermal shield is generally cylindrical shaped and has a center bore for receiving the intermediate conductive element. Typically, the electrically conductive spacer is cylindrical shaped and the intermediate conductive element is elongate. In some embodiments, the device further includes a disc-shaped electrode support that supports a conductive dome electrode portion shaped like a segment of a sphere (such as a hemisphere) formed on a surface of the electrode support. The electrode support may or may not form a part of the electrode. In some embodiments, the electrode support is integral with the electrode.

Certain embodiments of the first broad aspect include the elongate member comprising either a braided conductive layer, a metal layer with a helical configuration, or a metal tube with an interrupted helical groove cut into its outer surface. Other embodiments of the first broad aspect include the elongate member comprising non-metallic conductive materials.

In some embodiments of the electrosurgical device, the elongate member, the electrode, and the electrically insulative thermal shield have outer diameters that range from about 0.014 inches to about 0.050 inches. For some applications, embodiments of the device have dimensions (in particular outer diameter dimensions) that correspond with guidewire sizes to facilitate withdrawing the electrosurgical device from a patient during a procedure and exchanging it with a guidewire. Guidewires used in applicable procedures are typically selected from the group consisting of guidewires having an outer dimension of about 0.014 inches, 0.018 inches, 0.025 inches, 0.035 inches, and 0.038 inches. As an example, to facilitate exchange with a 0.035 inch guidewire, certain embodiments of the electrosurgical device include an elongate member with an outer diameter that ranges from about 0.033 inches to about 0.035 inches, the electrode having an outer diameter that ranges from about 0.032 inches to about 0.035 inches, and the electrically insulative thermal shield having an outer diameter that ranges from about 0.028 inches to about 0.031 inches. In a specific embodiment, the elongate member has an outer diameter of about 0.033 inches, the electrode has an outer diameter of about 0.032 inches, and the electrically insulative thermal shield has an outer diameter of about 0.028 inches. Embodiments can have dimensions corresponding to other guidewire sizes to facilitate exchange with other guidewires.

The electrosurgical device can further comprise a support wire or spine extending proximally from the electrically conductive spacer or another part of the electrosurgical device. The support spine adds stiffness and support to the elongate member, thereby facilitating advancement of the elongate member through body vessels. In general, there is no minimum spine length and the maximum support spine length is limited by the length of the lumen containing the spine. In some embodiments, the support spine can extend for a distance of about 3.835 inches (about 10 cm) or about 4 inches. In alternative embodiments, the support spine extends for a distance of at least about 3.835 inches (about 10 cm). In embodiments where a distal portion of the elongate member comprises a metal layer with cuts at least partially therethrough, the support spine can extend beyond the cut portion of the elongate member. In some embodiments, the support spine extends at least one centimeter proximal of the cut portion. Further details regarding the support spine are found in co-pending U.S. Provisional Patent Application Ser. No. 61/777,368, filed 12 Mar. 2013, previously incorporated by reference in its entirety.

In some embodiments, elongate member 6 is between about 50 cm and about 120 cm in length, as is the lumen 26 defined therein. In such embodiments, support spine can have a length between about 50 cm and about 120 cm. In embodiments of electrosurgical device 20 suitable for exchange, the length of elongate member 6 is between about 50 cm and about 250 cm, as is the length of the lumen 26 defined therein. In such embodiments, support spine can have a length between about 50 cm and about 250 cm in length.

Some embodiments of the first broad aspect include an electrosurgical device wherein the elongate member has a fixed length, and an energy delivery device with a substantially atraumatic tip.

In some embodiments of the first broad aspect, the thermal shield has a thermal conductivity of at least 1 W/m-K, and/or the thermal shield is a ceramic. In alternate embodiments, the thermal shield has a thermal conductivity of at least 2 W/m-K. Some embodiments of the electrosurgical device include a thermal shield comprising a material with a thermal conductivity ranging from about 1 W/m-K to about 5 W/m-K, for example, zirconium oxide and silicon carbide. Other embodiments of the electrosurgical device include a thermal shield comprising a material having a thermal conductivity ranging from about 15 W/m-K to about 40 W/m-K, for example, zirconia toughened alumina (ZTA), sapphire crystal (aluminum oxide), and silicon nitride.

In a second broad aspect, embodiments of the invention include a method to cross partial or total blockages with tough (calcified) caps, such as chronic total occlusions (CTOs), in vessels such as peripheral vessels. In some embodiments of this broad aspect, the method comprises the following steps: (1) injecting a contrast fluid through an electrosurgical device positioned adjacent an occlusion; (2) assessing visibility of one or more channels through the occlusion using an imaging modality; (3) if no channels are visible in step 2, delivering energy from the electrosurgical device to the occlusion; and (4) repeating steps (1)-(3), as needed, until one or more channels through the occlusion are visualized. The method typically further comprises a step of delivering energy to the one or more visualized channels using the electrosurgical device for creating a pathway through the occlusion.

Some embodiments of the second broad aspect include step (5) delivering contrast fluid after cutting through the blockage to confirm the crossing.

In a third broad aspect, embodiments of the invention include a method of cutting through an occlusion in a vessel of a patient, comprising the following steps: (i) positioning an electrosurgical device at a first desired location in the vessel substantially adjacent the occlusion; (ii) delivering energy using the electrosurgical device to at least partially cut through the occlusion; and (iii) measuring pressure using a pressure transmitting lumen defined by the electrosurgical device in order to determine the position of the electrosurgical device at least one of before and after step (ii). In some embodiments, step (i) comprises delivering contrast fluid through the electrosurgical device for confirming position at the first desired location. Some embodiments further comprise step (iv) advancing the electrosurgical device to a second location; and step (v) confirming position of the electrosurgical device at the second location using one or more of a pressure measurement through a pressure transmitting lumen defined by the electrosurgical device, or delivering contrast fluid through the electrosurgical device.

Other methods of using the electrosurgical device comprise delivering cooling fluid and/or electrolytes through the lumen and aperture, and/or measuring pressure through the lumen and aperture.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
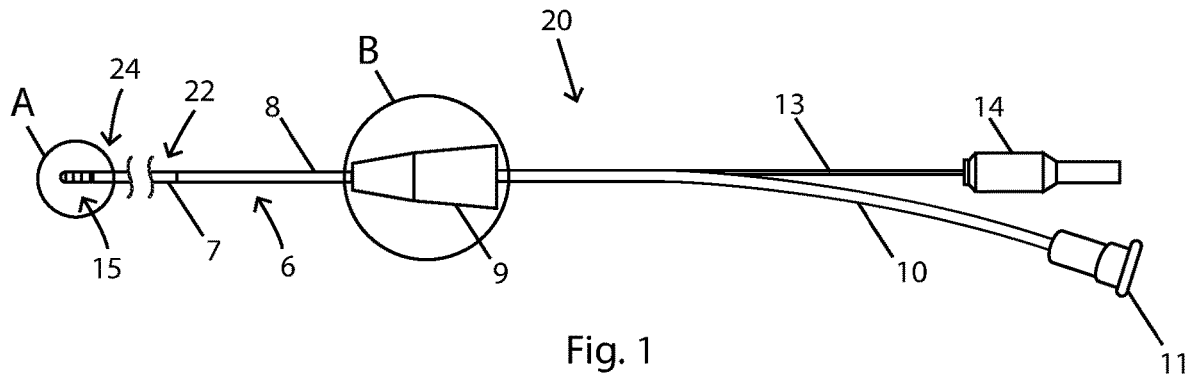
FIG. 1 is an illustration of an embodiment of an electrosurgical device of the present invention.

Current devices used for recanalization of chronic total occlusions (CTOs) are generally solid flexible wires, such as guidewires. Such devices typically lack means to deliver fluid for visualization during the recanalization procedure, which is one of the greatest challenges in CTO recanalization. As a solution, physicians commonly exchange the channeling device with a fluid delivery catheter, resulting in a cumbersome and time consuming procedure. Other challenges to CTO recanalization exist specifically when using a device to deliver electrical or thermal energy to the CTO. For example, the energy delivered for channeling may produce heat that may damage parts of the device close to the heating zone.

The inventors of the present application have conceived of, and reduced to practice, various embodiments of a device with features that address the above described challenges. The device includes a flexible elongate member comprised of an electrically conductive material. In addition, the elongate member defines a lumen suitable for fluid delivery, while remaining suitably dimensioned for traversing vasculature and channeling through an occlusion. The device is configured for delivering energy to an electrode through the side-wall of the elongate member such that it is not necessary to include a conductive wire within the lumen to provide energy to the electrode. This configuration leaves the fluid delivery portion of the lumen substantially free of obstruction, and enables the device to have a diameter suitable for delivery to, and channeling through, a CTO. Embodiments of the disclosed device further include a heat-shield between the electrode and the elongate member to protect the elongate member from heat damage.

In embodiments including an electrically insulative heat/thermal shield, the present inventors have further conceived and reduced to practice a means of maintaining a conductive pathway between the wall of the elongate member and the electrode. For example, the disclosed device also includes structure(s) defining the electrical pathway, where the structure(s) is/are small and structurally sound. The electrode and the structure(s) providing the pathway to the elongate member together form an energy delivery device. In some embodiments, an electrically conductive support spine extends from the energy delivery device proximally through a portion of the lumen to provide a secondary electrical path from the elongate member to the electrode. The support spine simultaneously provides structural support to the elongate member, particularly as the device bends or curves during use.

In addition, the present inventors have conceived of and reduced to practice novel methods of medical treatment. Some of the disclosed methods include channeling through chronic total occlusions within vasculature and delivering fluids using a single medical device rather than separate devices for energy delivery and fluid delivery.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1 illustrates an embodiment of a medical device 20 comprising an elongate member 6 with a proximal region 22 and a distal region 24, and an energy delivery device 15 associated with the distal end of device 20. Energy delivery device 15 is shown in greater detail in FIG. 2 and FIG. 5. Elongate member 6 is tubular in configuration, defining at least one lumen 26 extending substantially throughout its length (shown in FIG. 2), and is electrically conductive for conducting energy along its length to energy delivery device 15. In some embodiments, elongate member 6 is a hypotube. In addition, in typical embodiments, elongate member 6 defines at least one aperture 25 in a wall thereof (shown in FIG. 2). In typical embodiments, the aperture 25 is a distal aperture, i.e., an aperture at or near the distal end of elongate member 6 or medical device 20. The distal aperture and the lumen defined by the elongate member combine to form a pressure transmitting lumen, whereby fluid pressure from an external environment on the aperture is transmitted through a column of fluid located in the lumen to be measured at a proximal portion of the device. For example, the medical device may be operable to be coupled to a pressure sensing mechanism, such as a pressure sensor, to measure the pressure transmitted through the lumen. Medical device 20 further comprises a hub 9 associated with the proximal region 22 of elongate member 6 (shown in detail in FIG. 3). While the embodiment of elongate member 6 of FIG. 1 is biased towards a straight configuration, elongate member 6 is flexible enough to bend when advanced through a curved lumen. Some alternative embodiments of elongate member 6 include a curved portion (e.g. the embodiment of FIG. 7).

Figure 2:
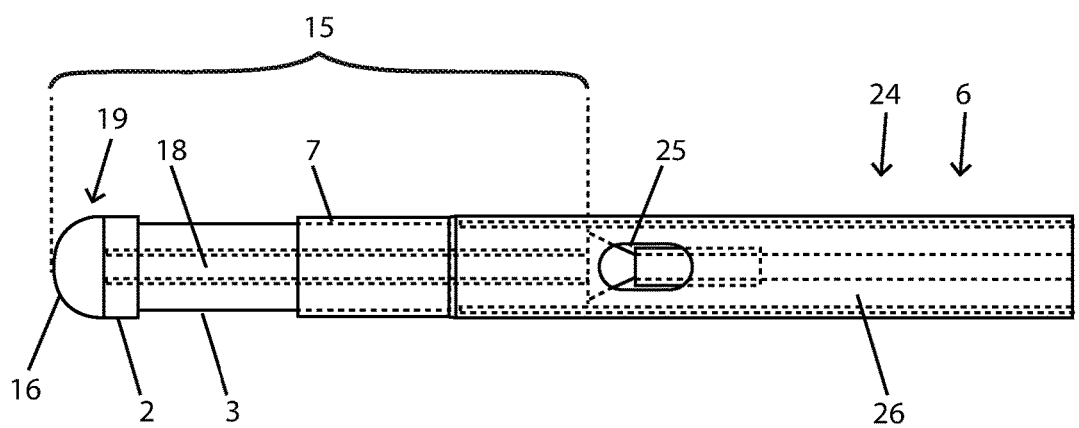
FIG. 2 is an illustration of detail A of FIG. 1.

FIG. 2 illustrates an embodiment of electrosurgical device 20 comprising insulation layer 7 disposed on top of, over, or around the distal region 24 of elongate member 6. Insulation layer 7 extends substantially from proximal region 22 to distal region 24 of elongate member 6. Insulation layer 7 may be made from an electrically insulative material such as PEBAX® (polyether block amide), PEEK (Polyether ether ketone), PTFE (Polytetrafluoroethylene), or another thermoplastic or polymeric material. In some embodiments, insulation layer 7 is at least partially pervious to light, for example, insulation layer 7 may be fabricated from a transparent Nylon. Insulation layer 7 may be applied to elongate member 6 by a variety of means. In one embodiment, insulation layer 7 is extruded over elongate member 6. In another embodiment, insulation layer 7 is manufactured as a pre-formed cylinder, which is placed over elongate member 6, and subjected to heat to tighten (i.e. recover) around elongate member 6. In another embodiment, insulation layer 7 is applied to elongate member 6 by dip-coating or spraying. As the outer diameter of elongate member 6 ranges from about 0.010 inches to about 0.050 inches, the inner and outer diameters of insulation layer 7 vary accordingly. In one embodiment, insulation layer 7 has a recovered inner diameter of about 0.028 to 0.030 inches and a recovered outer diameter of about 0.034±0.001 inches (recovered dimensions are the final dimensions after heat shrinking).

Electrical continuity exists between distal region 24 of elongate member 6 and electrode 19 of energy delivery device 15. As insulation layer 7 is present over substantially the entire elongate member, the path of least resistance for electrical energy flowing through elongate member 6 is through the electrode 19.

A thermal shield 3, located proximal of electrode 19, protects the integrity of the portion of device 20 proximal of electrode. Thermal shield 3 is an electrical and thermal insulator that functions to insulate and thus protect the distal region 24 of the elongate member (including insulation layer 7) from the heat generated at electrode 19. Thermal shield 3 also prevents arcing between the electrode and the elongate member. In typical embodiments of electrosurgical device 20, such as the example shown in FIG. 2, insulation layer 7 extends over (or overlaps) a proximal portion of thermal shield 3. Alternative embodiments do not include such an overlap.

Figure 9:
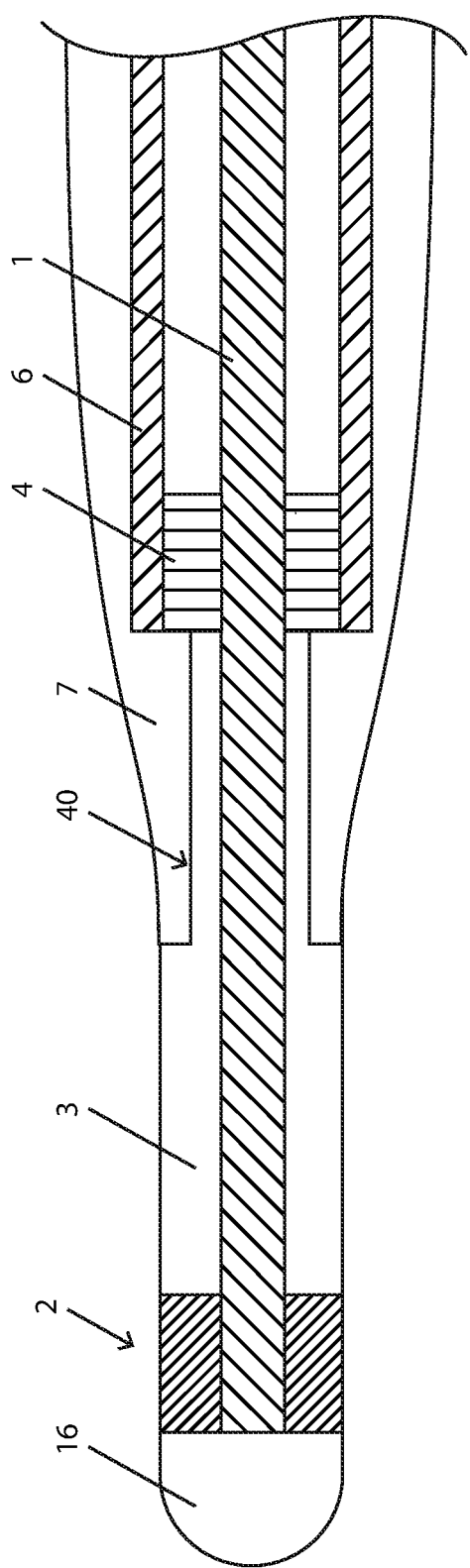
FIG. 9 is an illustration of an embodiment having a step-down or tapered thermal shield.

In embodiments with the above-described overlap of insulation layer 7, the overlap forms a sealed junction. This configuration may help minimize arcing observed proximal of the thermal shield 3 near the junction, and may help minimize degradation of insulation layer 7 from the heat generated by the delivery of electrical energy from the electrode to the surrounding tissue. The overlap of insulation layer 7 with thermal shield 3 can also prevent fluid from leaking from the distal portion of lumen 26. In some embodiments, thermal shield 3 can have a taper or step 40 to provide a smoother outer diameter transition between insulation layer 7 and thermal shield 3, as shown in FIG. 9. In some such embodiments, the taper or step 40 is substantially gradual, while in other embodiments the change in diameter is relatively discrete/abrupt.

Figure 8A:
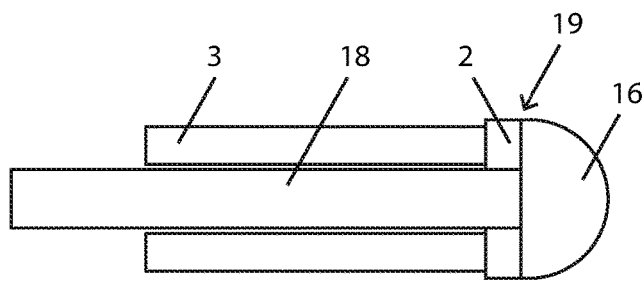
FIGS. 8A, 8B, 8C and 8D show an embodiment of the device that does not include a support spine.
Figure 8B:
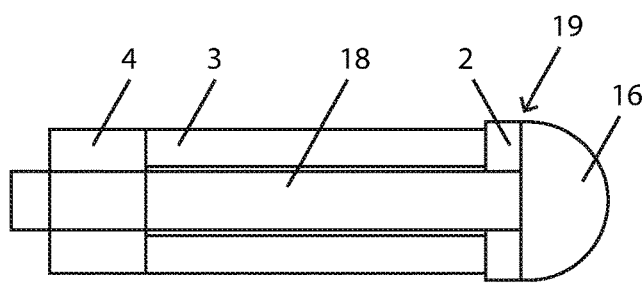
Figure 8C:
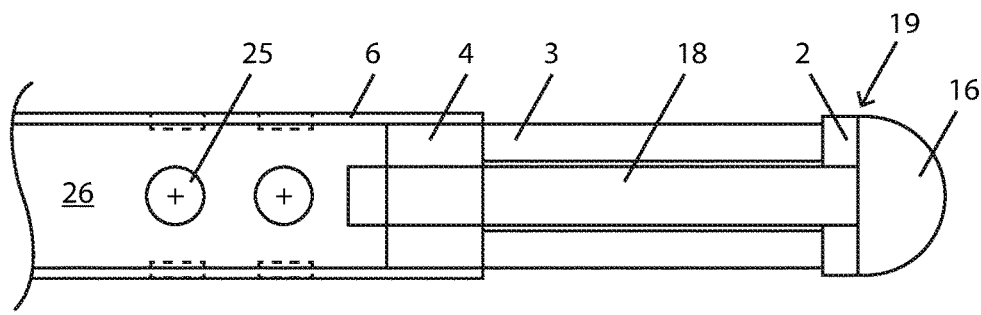
Figure 8D:
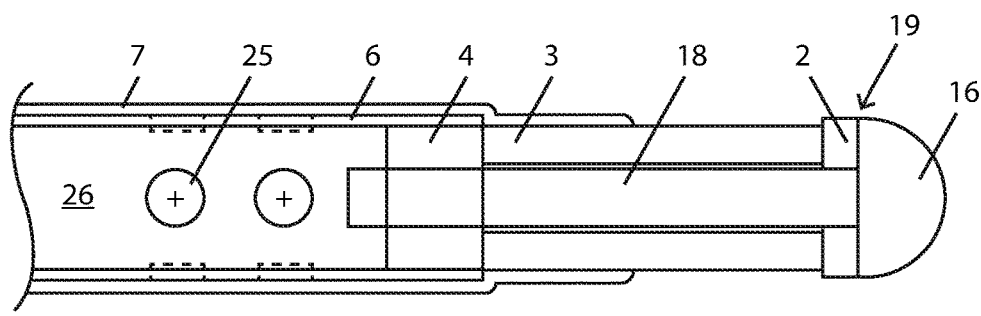

In some embodiments, elongate member 6 defines one or more apertures (or sideports) 25, as shown in FIGS. 2 and 8*d*. Aperture(s) 25 extend through insulation layer 7 and allow for fluid communication between the outside environment and lumen 26. For example, a physician using electrode 19 to cross (or channel through) an occlusion in a body vessel could inject a contrast fluid through lumen 26 and one or more apertures 25. Using x-ray fluoroscopy or another imaging modality, the physician could confirm how far the device has progressed in cutting or channeling through the occlusion. The apertures are typically large enough to allow fluid to flow through them.

In the embodiment of FIG. 1, proximal region 22 is coupled to a hub 9 (shown in detail in FIG. 3), which is coupled to flexible tubing 10 to establish fluid communication between the lumen 26 and a fluid connector 11. Flexible tubing 10 can comprise a polymeric material, for example, Tygon® tubing, polyvinylchloride (PVC), or another flexible polymer. Fluid connector 11 is structured to be operatively connected to a source of fluid, such as a syringe or an aspirating device, or to a pressure sensing device, such as a pressure transducer. Fluid connector 11 may be a Luer lock.

Electrosurgical device 20 further includes means for electrically coupling proximal region 22 of elongate member 6 to an energy source. In the embodiment of FIG. 1, proximal region 22 connects to hub 9 and insulated wire 13 is electrically coupled to proximal region 22 within hub 9. The proximal end of insulated wire 13 is connected to electrical connector 14 (or plug 14), which is electrically coupled to a source of energy, for example, a generator. Strain relief 8 (shown in FIGS. 1 and 3) provides for a transition of stiffness between proximal region 22 of elongate member 6 and hub 9.

Figure 3:
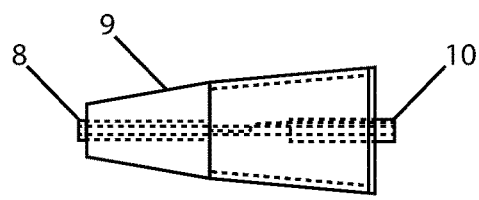
FIG. 3 is an illustration of detail B of FIG. 1.

Shown in detail in FIG. 3, hub 9 also functions as a handle for a physician when electrosurgical device 20 is in use. In some embodiments, the physician can remove the hub (or handle) 9 to allow proximal end loading of devices onto or into elongate member 6 for advancement thereupon or therethrough.

Figure 4:
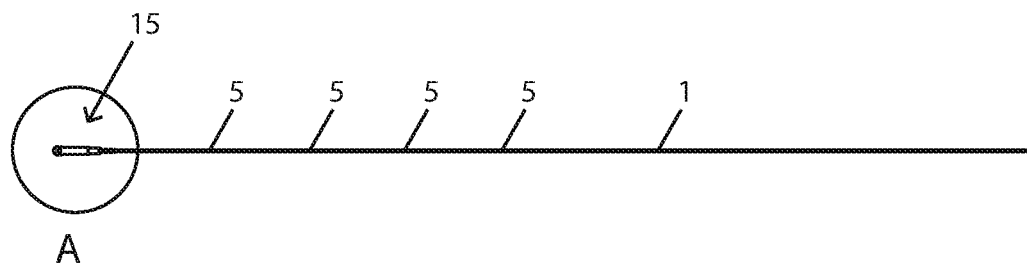
FIG. 4 is an illustration of a spine support and attached distal region of the energy delivery device of FIG. 1.
Figure 5:
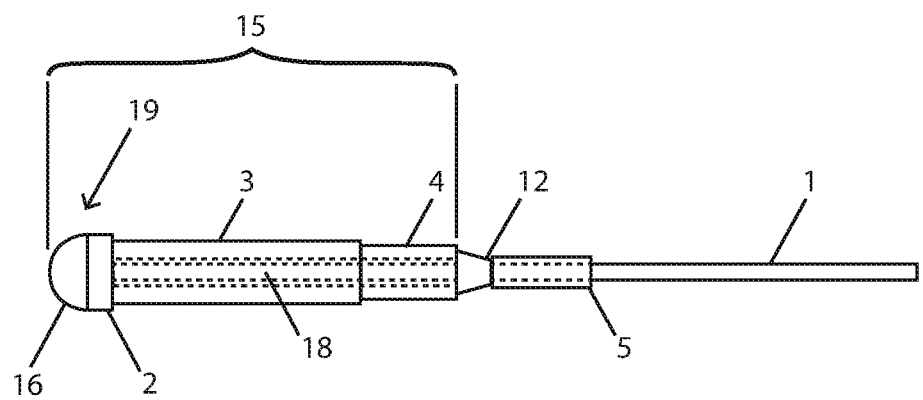
FIG. 5 is an illustration of detail A of FIG. 4.

Some embodiments of electrosurgical device 20 include a support spine 1 (also referred to as a support wire/stiffening member), as shown in FIGS. 4 and 5. Spine 1 functions to provide additional stiffness to electrosurgical device 20 while leaving lumen 26 substantially open or unobstructed for flow of fluid, such as imaging or contrast fluid. In some embodiments of electrosurgical device 20, the elongate member comprises a metal layer with a flexible helical configuration and the support spine 1 provides support to the wall of the elongate member. In some embodiments, spine 1 is comprised of nitinol and can provide shape memory properties to the electrosurgical device. In some embodiments incorporating a spine 1, the spine 1 is an electrical conductor that extends proximally from energy delivery device 15 to make an electrical connection with a conductive wall of lumen 26. In some such embodiments, spine 1 extends proximally beyond conductive spacer 4, and may extend for a distance of at least about 10 cm. In some such embodiments, the support spine extends proximally for a distance in a range of between about 10 cm to about 120 cm. In other embodiments, support spine extends proximally for a distance in a range of between about 10 cm to about 250 cm. In alternative embodiments, spine 1 is electrically non-conductive.

In the embodiment illustrated in FIG. 5, spine 1 includes a flare 12 (or a barb) to retain conductive spacer 4 in place. In some embodiments, flare 12 is separate from and coupled to spine 1, while in alternative embodiments flare 12 is integral with spine 1. In embodiments that lack a flare 12, a band marker 5 (as described further herein below) could be positioned adjacent conductive spacer 4 to retain the spacer in place.

Further details regarding the support spine are found in co-pending U.S. Provisional Patent Application Ser. No. 61/777,368, filed 12 Mar. 2013, previously incorporated by reference in its entirety.

Some embodiments, such as the embodiment of FIG. 5, include an intermediate conductive element 18 for conducting electrical energy between components of the electrosurgical device, for example, between electrode 19 and spine 1. In some such embodiments, intermediate conductive element 18 is an extension of spine 1. In alternative embodiments, intermediate conductive element 18 is a separate part distinct from spine 1, such as a wire or rod.

In some embodiments, one or more visualization markers, such as radiopaque markers 5 shown in FIGS. 4 and 5, highlight the location of important landmarks on electrosurgical device 20 when viewed using a medical imaging modality. Such landmarks may include the location of energy delivery device 15 or the location of any aperture(s) 25. Typically, radiopaque markers 5 provide the radiopacity to more readily visualize the device under fluoroscopy. Radiopaque marker 5 can be a band marker comprised of platinum or any other suitable radiopaque material. In alternative embodiments, other forms of markers are employed for visualization using alternate imaging modalities. For example, echogenic markers are utilized to enable visualization using ultrasonic imaging.

Figure 14A:
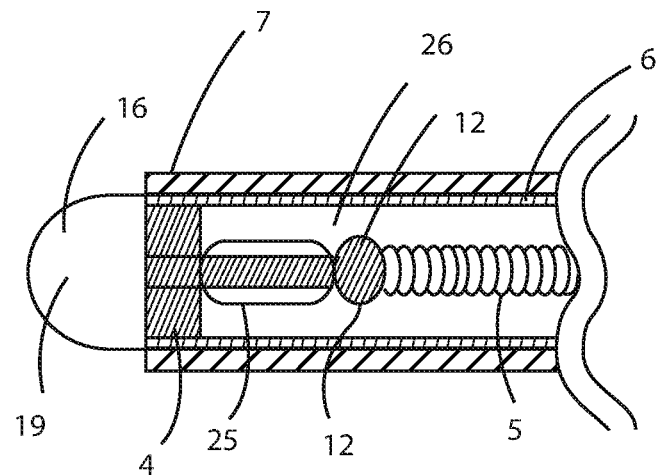
FIGS. 14A and 14B illustrate embodiments having coiled markers.
Figure 14B:
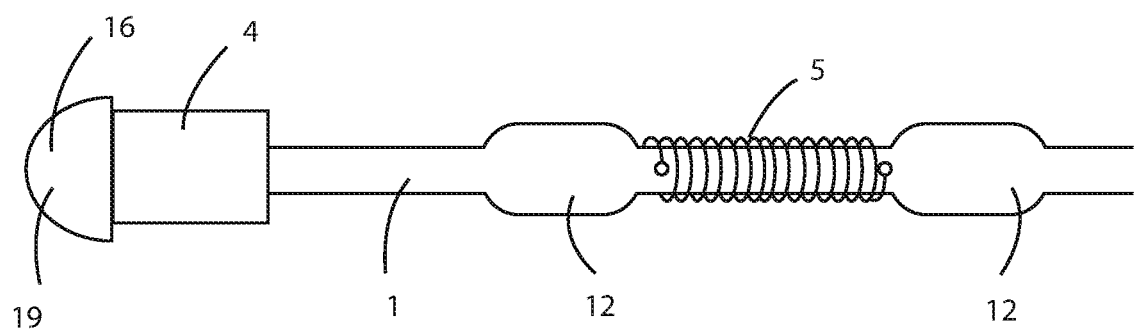

Some alternative embodiments have a spiral or a coiled marker 5 rather than band markers. A coiled marker 5 is typically comprised of platinum or tungsten. In the embodiments of FIGS. 14A and 14B, coiled markers 5 are installed on spine 1. Each flare 12 acts as a restraint to prevent coiled marker 5 from travelling along spine 1. In the embodiment of FIG. 14B, each flare 12 is comprised of a flattened portion of spine 1. In alternative embodiments, one or both ends of a coiled marker could be fixed in place by laser welding or crimping. In the embodiment of FIG. 14A, the coiled marker is proximal of the aperture 25 in order to indicate the position of the aperture within a patient's body to the operator during use. For example, if the operator views the coiled marker 5 outside of a dilator (i.e. distal to the dilator tip), he/she can be assured that aperture 25 is also outside of the dilator and can be used to deliver or aspirate fluids, and/or measure pressure.

Figure 16A:
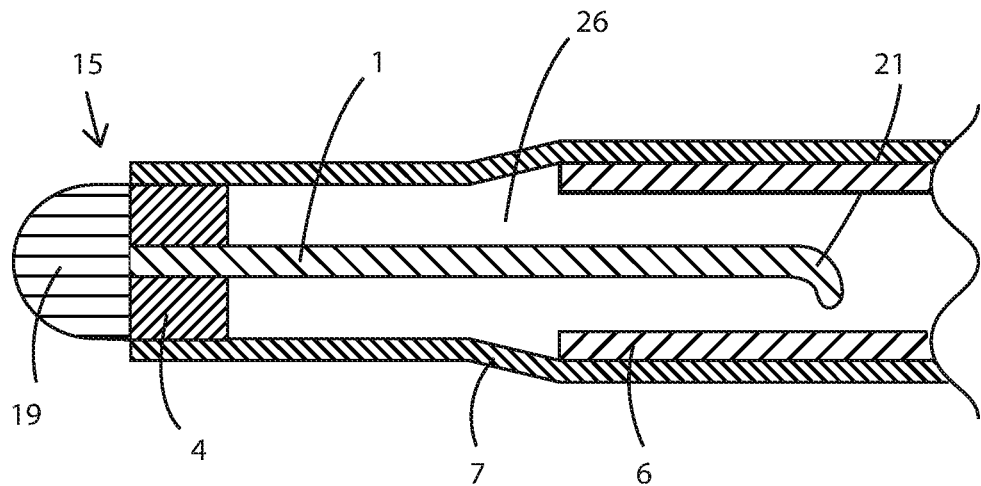
FIGS. 16A and 16B illustrate embodiments with electrically conductive spines.
Figure 16B:
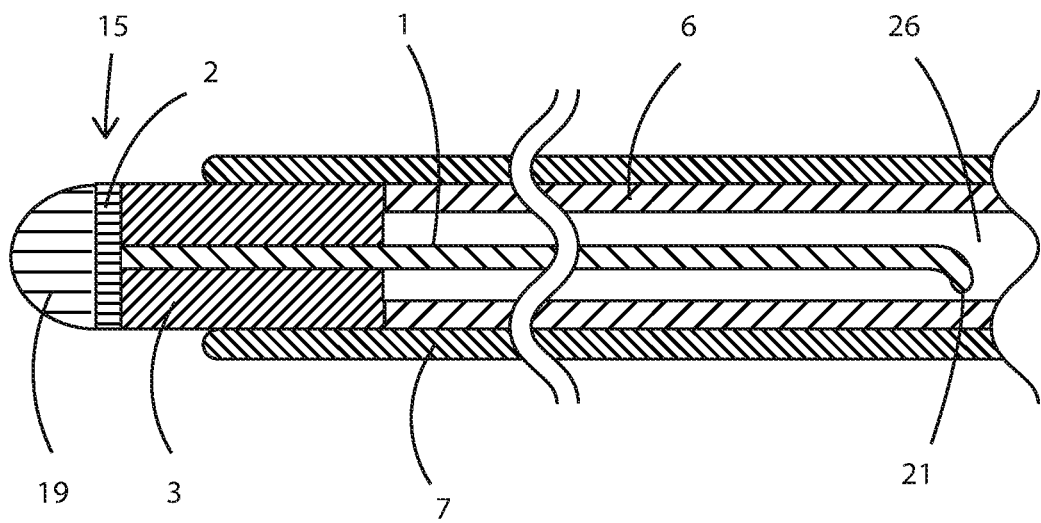

Energy delivery device 15 of the embodiment of FIG. 5 is comprised of an electrode 19, an intermediate conductive element 18 attached to and in electrical communication with electrode 19, and a conductive spacer 4 attached to and in electrical communication with intermediate conductive element 18. While different configurations of electrode 19 are possible, FIG. 5 discloses an embodiment including support structure 2 and a conductive dome 16. In addition, while FIG. 5 illustrates an energy delivery device associated with a spine 1, other embodiments incorporate an energy delivery device 15 without a spine 1. Support structure 2 can be metallic, puck or disk-shaped and, in some embodiments, is comprised of tantalum. Conductive spacer 4 may be comprised of materials such as Nitinol, gold, stainless steel, and platinum. Conductive dome 16 may be formed by laser welding a metal, such as the end of intermediate conductive element 18, onto support structure 2. In alternative embodiments, conductive spacer 4 is replaced by other energy delivery device coupler elements for attachment of energy delivery device 15 to elongate member 6. In some such embodiments, the energy delivery device coupler comprises an electrically conductive support spine (as shown in FIG. 16B).

Electrode 19 is configured and sized to provide a current density at electrode 19 sufficient to generate arcing in a region of tissue when electrode 19 is positioned proximate the region of tissue. This arcing creates a channel through at least a portion of the region of tissue. For details regarding electrosurgical arcing and channel creation, reference is made to U.S. patent application Ser. No. 12/926,292, previously incorporated herein by reference in its entirety.

As illustrated in FIG. 5, thermal shield 3 is mounted about intermediate conductive element 18. In some embodiments, thermal shield 3 is a ceramic, for example, sapphire, zirconia, or alumina. Intermediate conductive element 18 is comprised of any suitable conductive material that is electrically coupled to the other components of electrosurgical device 20 as described herein.

Electrode 19 is electrically and operatively coupled to energy delivery device 15 by a variety of means, for example, gluing or insert molding. The electrode is made from any suitable electrically conductive material. Examples of suitable materials include stainless steels, copper, and platinum.

The electrode may be one of various shapes and sizes, for example, substantially cylindrical, and/or having a hemispherical, rounded, or domed end.

Making reference to FIGS. 2 and 5, the wall of elongate member is operable to conduct energy (such as electrical energy), eliminating the need for a separate conductive element (such as a wire) to be located within lumen 26. This configuration allows sufficient space in lumen 26 for fluid to travel and flow through apertures 25. (In some embodiments, support spine 1 may be an electrical conductor, however it is typically located in the distal end of lumen and does not substantially obstruct fluid flow throughout lumen 26). In some such embodiments, electrode 19 is electrically coupled to an inner wall of elongate member 6 while the insulation layer 7 is thermally insulated from electrode 19 by means previously described (e.g. using thermal shield 3). Thus, a single electrosurgical device 20 with an outer diameter between about 0.014 inches to about 0.050 inches, such as the embodiments of FIGS. 2 and 5, can adequately deliver both energy and fluid to a target location within a patient's body.

In some embodiments, elongate member 6 is fabricated from a super-elastic material, which facilitates the advancement of electrosurgical device 20 through tortuous vasculature.

Elongate member 6 is electrically coupled to energy delivery device 15 by a variety of connecting means. For example, in one embodiment, elongate member 6 can be welded or soldered to conductive spacer 4 of energy delivery device 15.

Embodiments of elongate member 6 are made from a number of different materials. Examples include stainless steel, copper, nickel, titanium, and alloys thereof. In some embodiments, elongate member 6 comprises a stainless steel hypotube or a nitinol hypotube.

In some embodiments, notches are cut into elongate member 6, for example, by laser-cutting. The region comprising the notches retains conductivity along elongate member 6, but is relatively more flexible than it would be without such cuts. Different configurations of cuts are possible, including c-cuts, spiral shaped cuts, interrupted spiral cuts, interlocking cuts, and dove-tail cuts. The cuts or notches may be made partially or completely through a wall of elongate member 6.

Figure 6:
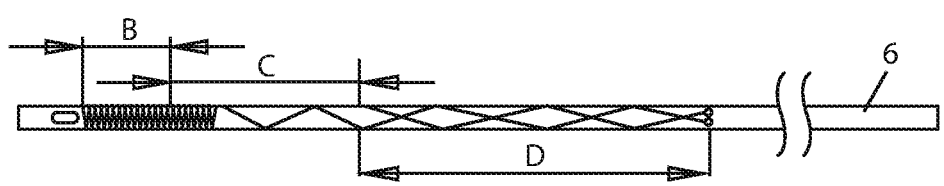
FIG. 6 is an illustration of an embodiment of an elongate member comprising a hypotube with cuts therein.

The specific embodiment of FIG. 6 discloses cuts into elongate member 6 that include constant pitch portion B, variable pitch portion C, and dual pitch potion D. Elongate member 6 of FIG. 6 may be a hypotube. The cuts into the hypotube may traverse the hypotube wall. Having a smaller pitch (i.e. having the cuts closer together) increases the flexibility of elongate member 6. For example, the distal part of variable pitch portion C has a smaller pitch than the proximal part of variable pitch portion C and consequently is more flexible. Portion D has a dual pitch (i.e. two cut lines), which further increases the flexibility of elongate member 6 in that portion.

This variable flexibility assists in the proper positioning and use of electrosurgical device 20 in surgical procedures. For example, a more flexible distal region 24 is desirable for navigating through conduits in a patient's body, such as blood vessels, while a stiffer proximal region 22 is desirable for pushability of the device and resistance to kinking under axial compression force. A relatively stiffer proximal region 22 is desirable for torque response and radial rigidity. The flexibility of an embodiment of elongate member 6 depends on its wall thickness and/or outer diameter. Different embodiments of the elongate member 6 may have different wall thicknesses and/or different outer diameters in order to create a device with the desired flexibility. To vary flexibility along the length of the elongate member 6, alternative embodiments of elongate member 6 may have varying wall thickness with a constant outer diameter along its length, and/or varying outer diameter with a constant wall thickness along its length.

In some embodiments of electrosurgical device 20 incorporating a spine 1 in which elongate member 6 is biased to be straight, the shape memory properties and stiffness of spine 1 compensate for the flexibility created by cuts into the elongate member 6. These characteristics of spine 1 also allow electrosurgical device 20 to display the stiffness and response of a guidewire, and revert to a straight configuration after bending. In addition, spine 1 can act as a bridge across the cuts to distribute the bending stress along elongate member 6, as described with reference to FIGS. 25A and 25B of U.S. Provisional Patent Application Ser. No. 61/777, 368.

In some embodiments, the length of elongate member 6 is between about 50 cm and about 120 cm, and has an inner diameter of about 0.028 inches and an outer diameter of about 0.032 inches. Embodiments of this length have a fixed (i.e. not removable) hub (or handle). Other embodiments have an inner diameter of about 0.025 inches and an outer diameter of about 0.029 inches. The dimensions of elongate member 6 depend on factors such as the distance to the target site, the tortuosity and/or diameter of the vessel(s) to be navigated, whether or not the elongate member is desired to be exchange length, and any other requirement imposed by auxiliary devices to be used with elongate member 6. For example, elongate member 6 is typically sized to be compatible with a particular sheath and/or dilator.

Figure 7:
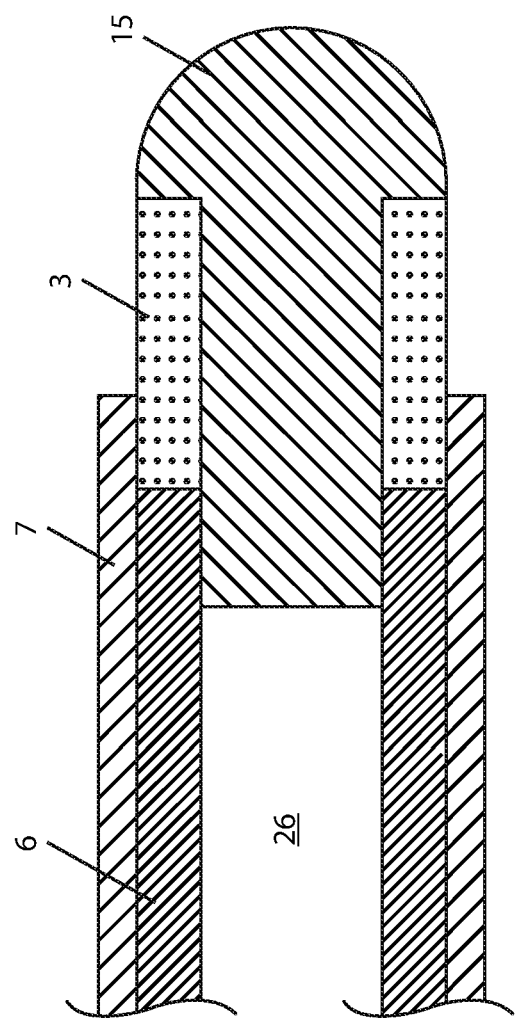
FIG. 7 is an illustration of an embodiment with an integral (single piece) energy delivery device.

Alternative configurations of the energy delivery device 15 are possible. The embodiment of FIG. 7 illustrates an example of an integral (single piece) energy delivery device 15. The embodiment combines the conductive spacer 4, intermediate conductive element 18, and electrode 19 into a single, unitary energy delivery device 15. In some such embodiments, thermal shield 3 is attached to energy delivery device 15 by gluing or pressure fit, and/or is retained in place, at least in part, by insulation layer 7.

FIGS. 8A, 8B, 8C and 8D disclose an embodiment of the electrosurgical device 20 without a support spine. The embodiment includes an intermediate conductive element 18 comprising a metal rod. The electrosurgical device is configured to allow the flow of electrical energy through the wall of elongate member 6, through conductive spacer 4, and through intermediate conductive element 18 to tip electrode 19. The embodiment also permits the delivery and/or aspiration of fluid through lumen 26 and aperture(s) 25, and lacks an extended support spine, thereby further facilitating fluid flow through lumen 26. This particular embodiment includes eight circular apertures (six are shown in the figures, with another two in the wall that is cut-away in the figures) but the number and shape of aperture(s) 25 can vary.

In some embodiments of medical device 20, the support spine 1 functions as the primary (or only) pathway for electrical energy to travel from elongate member 6 to energy delivery device 15. In the example of FIG. 16A, conductive spacer 4 is spaced apart from and not in contact with elongate member 6. Insulation layer 7 is a continuous layer of one material in the embodiment of FIG. 16A, but in alternative embodiments, insulation layer 7 could be comprised of more than one type of material. For example, the portion of insulation layer 7 covering elongate member could be one or more type(s) of material, and the portion of insulation layer 7 distal of elongate member 6 could a different material (or materials). In general, at least some portion of insulation layer 7 distal of elongate member 6 is comprised of electrically non-conductive material, whereby electrical energy cannot flow through insulation layer 7 to energy delivery device 15.

The embodiment of FIG. 16A includes a spinal curve 21 at the proximal end of support spine 1 to facilitate contact between support spine 1 and elongate member 6. Other embodiments of medical device 20 could have a bent support spine 1, a generally straight support spine 1, or a support spine 1 with another configuration, for example, a helical spring. Whether the proximal portion of support spine 1 is curved, bent, straight, or another configuration, support spine 1 is typically sufficiently elongate and floppy to contact elongate member 6 at some position along its length. While conductive spacer 4 is typically metallic to facilitate welding electrode 19 to medical device 20 and securing support spine 1, in alternative embodiments, conductive spacer 4 could be a non-metallic material and/or an electrically non-conductive material.

Making reference to FIG. 16B, some embodiments of medical device 20 have a thermal shield 3 comprised of non-conductive material whereby support spine 1 functions as the primary pathway for electrical energy to travel from elongate member 6 to energy delivery device 15. While thermal shield 3 is a single integral part in the embodiment of FIG. 16B, in alternative embodiments, thermal shield 3 could be comprised of more than one part and/or material. The embodiment of FIG. 16B does not include a conductive spacer 4 proximal of thermal shield 3, unlike the embodiment of FIG. 5 which has a conductive spacer 4 to enable electrical communication between elongate member 6 and electrode 19. Some embodiments include an energy delivery device 15 comprised of support structure 2 and electrode 19, such as the example of FIG. 16B, while alternative embodiments may have an energy delivery device 15 comprised of a single integral part, or an energy delivery device 15 with another configuration. While the embodiment of FIG. 16B includes a spinal curve 21, alternative embodiments of medical device 20 have a proximal portion of support spine 1 that is bent, straight, or another configuration. Alternative embodiments include a flare 12, as previously described in reference to FIG. 5. In both of the embodiments illustrated in FIGS. 16A and 16B, a non-conductive material restricts or impedes the electrical pathway from elongate member 6 to electrode 19 such that support spine 1 is the primary (or only) pathway of electrical conductivity between elongate member 6 and electrode 19. The non-conductive material could be, for example, a ceramic or a polymer.

Medical device 20 may be used in conjunction with a source of energy suitable for delivery to a patient's body. Sources of energy include generators of ultrasonic, microwave, radiofrequency, or other forms of electromagnetic energy. In embodiments utilizing ultrasonic energy, energy delivery device 15 may comprise an ultrasound transducer. In one particular embodiment, the source of energy is a radiofrequency (RF) electrical generator, such as a generator operable in the range of about 100 kHz to about 3000 kHz, designed to generate a high voltage in a short period of time. More specifically, the voltage generated by the generator may increase from about 0 Vrms to greater than about 400 Vrms in less than about 0.6 seconds. The maximum voltage generated by the generator may be between about 180 V peak-to-peak and about 3000 V peak-to-peak. The waveform generated may vary, and may include a sine-wave or a rectangular wave, amongst others. In some embodiments, the impedance encountered during RF energy application may be very high due to the small size of the electrode. The generator is operable to deliver energy notwithstanding the increased impedance, and may be operable to maintain the desired voltage even with low or fluctuating tissue impedance. Output impedance of a suitable generator may be between 100 ohm and 200 ohm. In one particular example, energy is delivered to a tissue within a body at a voltage that rapidly increases from 0 Vrms to 400 Vrms. Alternate embodiments of suitable radiofrequency generators have power capabilities of 0 to 25 watts, 0 to 50 watts, or 0 to 300 watts.

In one broad aspect, electrosurgical device 20 is used to deliver energy to a target site within a body of a human or animal while concurrently or sequentially delivering a fluid via aperture(s) 25.

In some embodiments, the energy may be radiofrequency (RF) current, and the energy may puncture or create a void or channel in the tissue at the target site. An operator uses the medical device 20 to deliver RF energy to a target tissue to create an insulative vapor layer around the electrode, thereby resulting in an increase in impedance. For example, the impedance may increase to greater than 4000Ω. Increasing the voltage increases the intensity of fulguration, which may be desirable as it allows for an increased tissue puncture rate. An example of an appropriate generator for this application is the BMC RF Puncture Generator (Model numbers RFP-100 and RFP-100A, Baylis Medical Company, Montreal, Canada). These generators can deliver continuous RF energy at about 480 kHz. A grounding pad or dispersive electrode is connected to the generator for contacting or attaching to a patient's body to provide a return path for the RF energy when the generator is operated in a monopolar mode.

Further details regarding delivery of energy to a body may be found in U.S. patent application Ser. No. 10/347,366 (filed on Jan. 21, 2003), Ser. No. 10/760,749 (filed on Jan. 21, 2004), Ser. No. 10/666,288 (filed on Sep. 19, 2003), and Ser. No. 11/265,304 (filed on Nov. 3, 2005), and U.S. Pat. No. 7,048,733 (application Ser. No. 10/666,301, filed on Sep. 19, 2003), all of which are incorporated herein by reference.

In some embodiments, electrosurgical device 20 may be used to create a channel through an occluded lumen or other material within the body. Examples may include blood vessels, stent-graft fenestrations, the bile duct, or airways of the respiratory tract. An occlusion may comprise fibrous tissue or other material, and the occlusion may be partial or substantially complete. In some embodiments, electrosurgical device 20 is positioned such that the electrode is adjacent the material to be punctured. Energy may be delivered from a source, such as a generator, via elongate member 6, to the target site such that a void, or channel, is created in or through the tissue. Further details regarding delivery of energy to create channels through tissue or occlusions may be found in U.S. patent application Ser. No. 12/926,292, filed on Nov. 8, 2010, U.S. patent application Ser. No. 13/286,041, filed on Oct. 31, 2011, and U.S. Pat. No. 8,048,071, issued Nov. 1, 2011 previously incorporated herein by reference.

Figure 10:
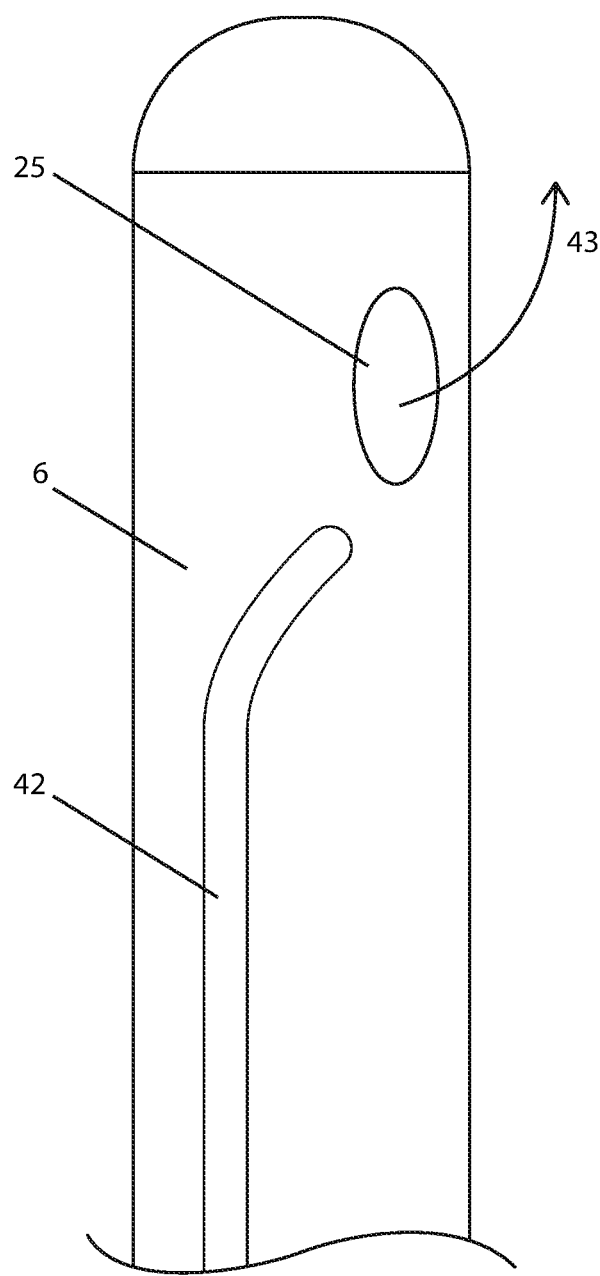
FIG. 10 illustrates the travel path of a wire through an electrosurgical device.

After crossing an occlusion with electrosurgical device 20, an operator can replace device 20 with a guidewire prior to installation or insertion of a separate device used for widening the puncture or channel, such as a dilator or balloon catheter. In one method of using electrosurgical device 20, an operator can install a guidewire 42, such as a wire with a curved or bent distal end, through lumen 26 of electrosurgical device 20 and out of an aperture 25, as indicated by arrow 43 in FIG. 10. The operator can advance the wire 42 under imaging, and when the distal end of wire 42 has advanced sufficiently to reach aperture 25, the operator may rotate the wire 42 if required to locate aperture 25. The operator can then remove the electrosurgical device 20 from the body, and insert a dilation device over wire 42. Alternatively, the operator can load widening devices onto or over electrosurgical device 20, in front of (i.e. distal to) hub 9, prior to inserting device 20 into the vasculature and/or prior to utilizing device 20 to cross the occlusion. As previously described, it is also possible to use an electrosurgical device with a removable hub 9 to facilitate proximal-end loading of devices onto electrosurgical device 20.

In some embodiments, a method of the present invention includes delivering contrast or imaging fluid to the treatment site to provide the physician with information about the environment using a medical imaging modality. For example, under fluoroscopy, an operator can inject contrast fluids into CTOs in the coronary vessels to expose microvessels that may be used as pathways within the occlusion.

Figure 11A:
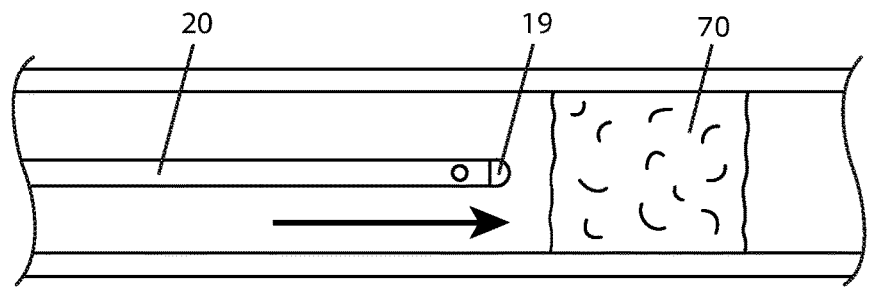
FIGS. 11A, 11B, 11C, 11D, 11E and 11F illustrate the steps of an embodiment of a method that includes delivering contrast fluid.
Figure 11B:
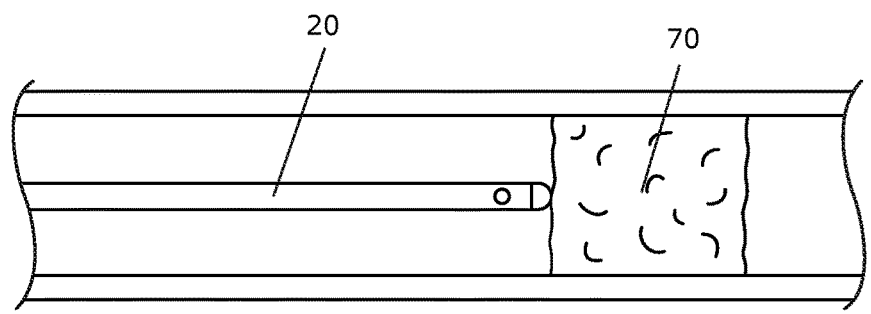
Figure 11C:
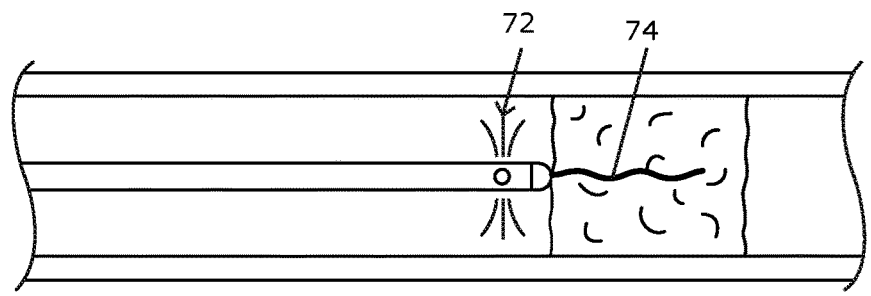
Figure 11D:
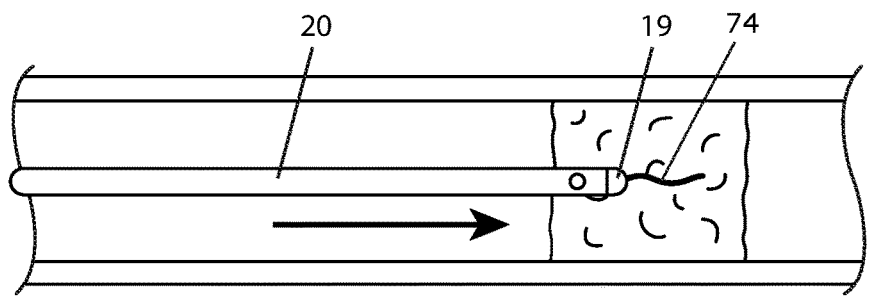
Figure 11E:
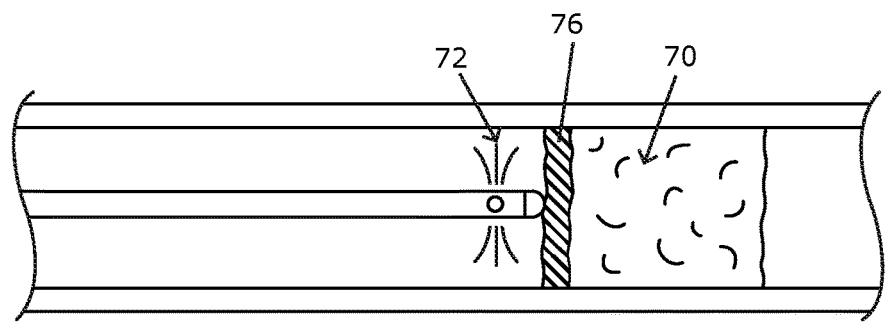
Figure 11F:
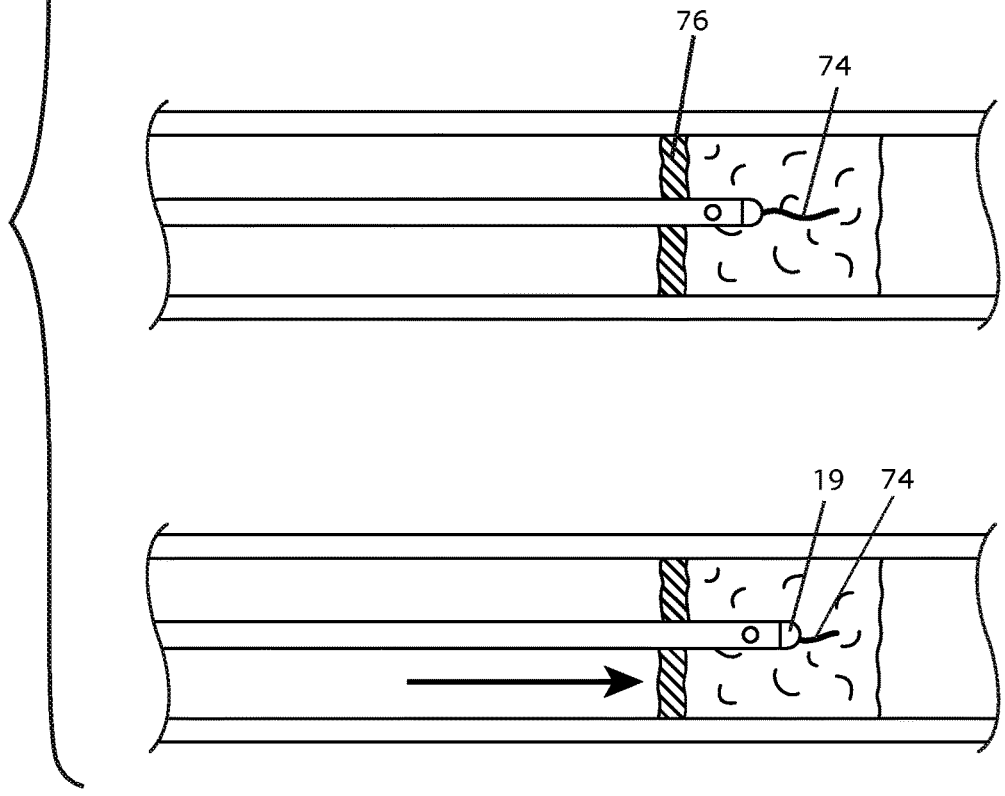

Some CTOs have tough proximal caps that are difficult to cross. Referring to FIGS. 11A to 11F, an embodiment of a method of crossing CTOs in peripheral vessels that may have tough (calcified) caps comprises the following steps: (1) inserting electrosurgical device 20 into the vessel and advancing to the CTO 70 site in the vessel (FIG. 11A); (2) engaging the CTO 70 (FIG. 11B); (3) injecting contrast fluid 72 and checking for channels 74 through the occlusion using fluoroscopic imaging (FIG. 11C or 11E); (4a) if pathways or channels 74 are seen, using them as a guide to cut through the CTO by delivering energy through electrode 19 (FIG. 11D); and (4b) if no pathways are seen in step (3), delivering energy through electrode 19 to cut through the proximal cap 76 (which may prevent contrast fluid from accessing any microchannels), injecting additional contrast fluid after the proximal cap is traversed, and, if pathways 72 are visible, using any such visible pathway 72 as a guide to cut through the remainder of the CTO 70 by delivering energy through electrode 19 (FIG. 11F). If no pathways are visible, continue delivering energy as the device advances through the occlusion. These steps may be repeated in order to check for pathways through the occlusion as the device is advanced.

After the steps described in the above method are completed and the CTO is crossed, more contrast fluid can be delivered to confirm the crossing.

Figure 12:
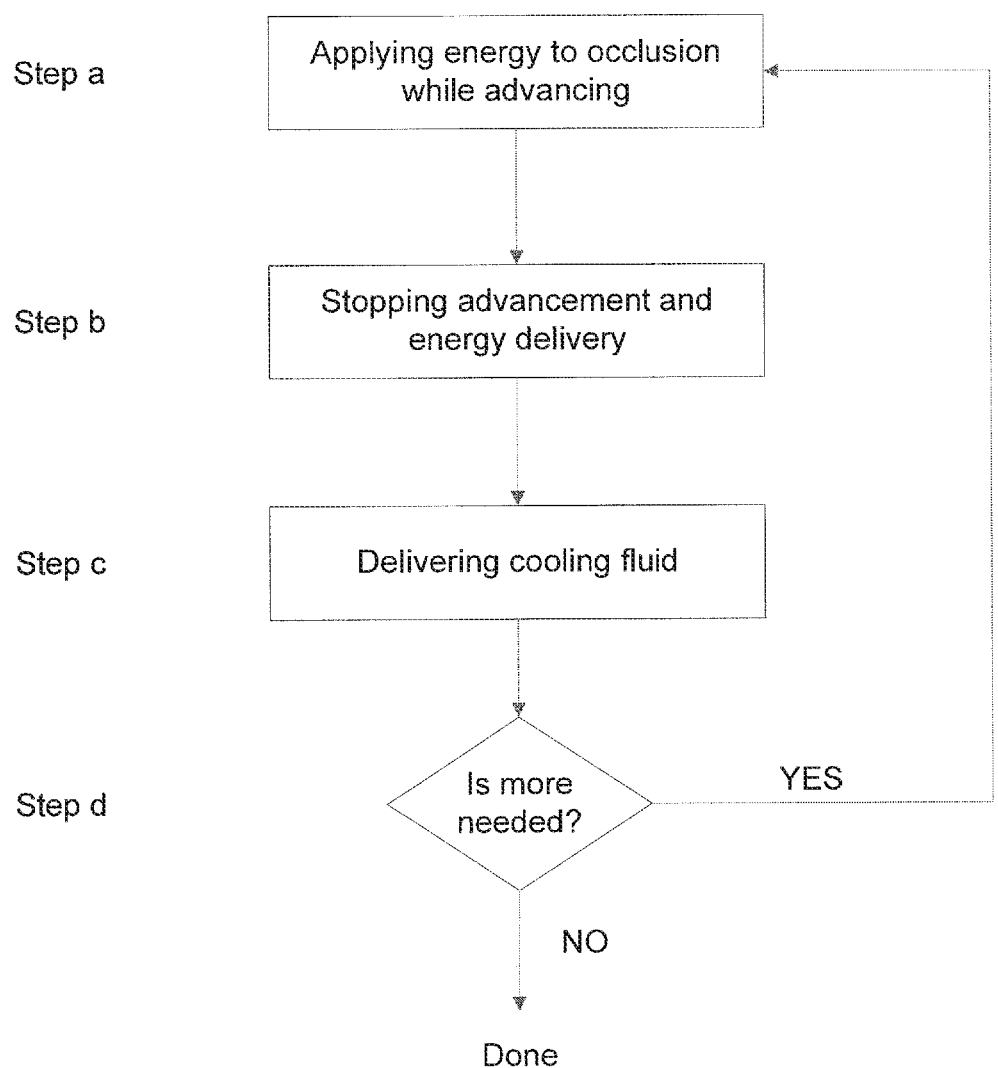
FIG. 12 is a flow chart of an embodiment of a method that includes delivering cooling fluid.

Some methods of using electrosurgical device 20 to cross CTOs or other occlusions or stenoses include delivering fluid for cooling the tissue around the occlusion to avoid heat damage to the tissue surrounding the electrode. FIG. 12 illustrates an embodiment of such a method comprising the following steps: (a) applying RF energy to the occlusion through electrode 19 while advancing electrosurgical device 20, (b) stopping advancement of electrosurgical device 20 and the application of energy, (c) delivering about 1 cc to about 2 cc of cooling liquid to the treatment site, and (d) repeating steps (a) through (c) as needed. In some embodiments, the generator used to supply the energy in step (a) can be set at power levels ranging from about 0 W to about 70 W. In some embodiments of the method, energy is delivered for a time period from about 50 microseconds to about 5 seconds. Some embodiments include multiple or pulsed deliveries of energy. Energy is delivered at power levels and time periods appropriate for the occlusion and surrounding tissue. The fluid delivered for cooling in step (c) may include bio-compatible saline. Some embodiments of a method aspect of the present invention include delivering contrast fluid for imaging during step (c). In the embodiment of FIG. 12, energy and fluid delivery are sequential.

Other methods of using electrosurgical device 20 to cross CTOs include delivering energy on a substantially continuous and constant basis, while advancing and delivering cooling fluid at least partly concurrently with the delivery of energy. In such embodiments, energy delivery is maintained while fluid delivery may be stopped or started during the procedure. Thus, at certain points in the procedure energy and fluid are delivered simultaneously, while at other points only energy is delivered.

Further methods of using electrosurgical device 20 to cross occlusions such as CTOs include continuously delivering fluid while advancing the device, and delivering energy as needed. The energy can be delivered continuously or intermittently. In such embodiments, delivery of fluid is maintained, while the delivery of energy may be terminated or initiated during the procedure. As in the previous embodiment, at certain points in the procedure energy and fluid are delivered simultaneously, while at other points only fluid is delivered. Discontinuous delivery may include delivering energy or fluid in short pulses, repeating longer periods of delivery, or intermittent delivery controlled by the physician.

Figure 13:
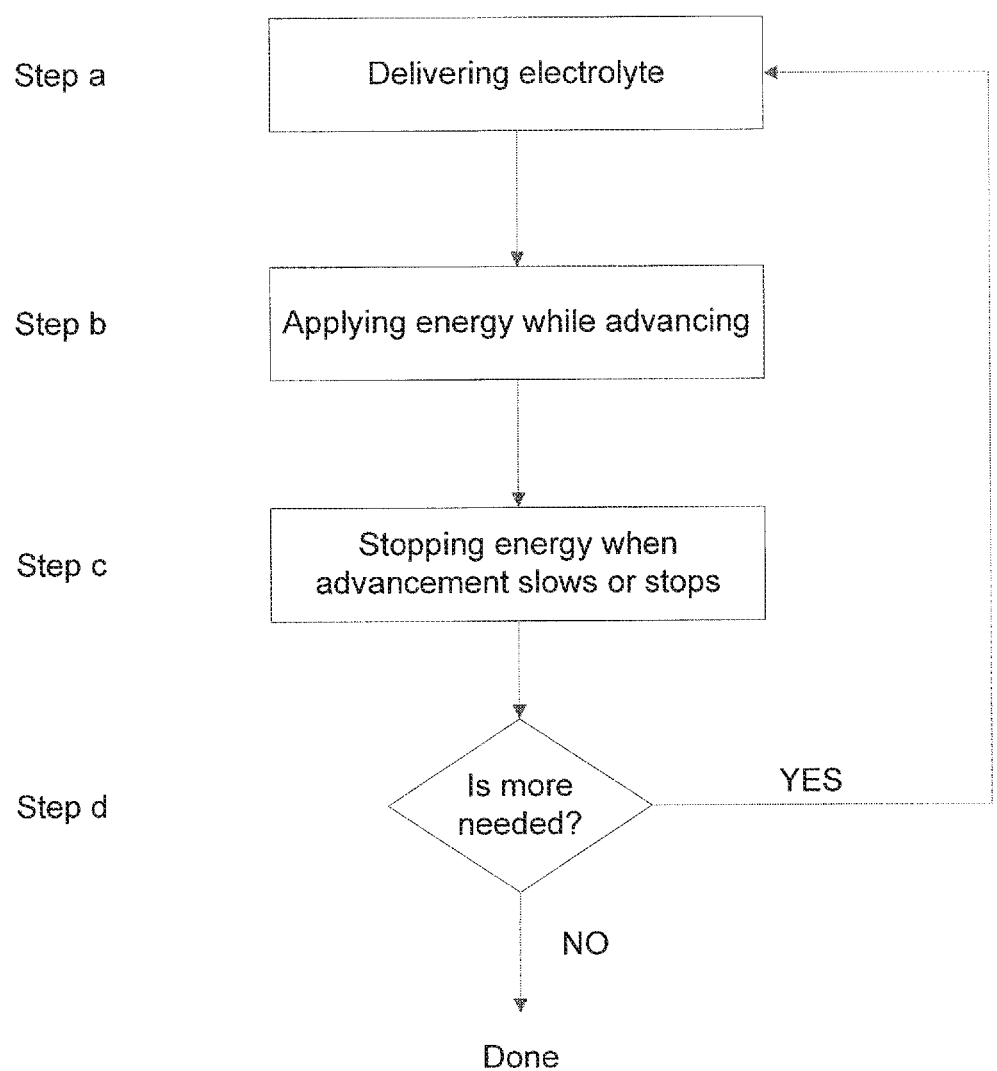
FIG. 13 is a flow chart of an embodiment of a method that includes delivering an electrolyte.

Injected fluid (such as saline) may also serve as an electrolyte to improve the efficacy of the energy delivered to puncture the tissue. FIG. 13 illustrates one embodiment of a method of using electrosurgical device 20 to cross occlusions such as CTOs that includes delivering electrolyte fluid to the treatment site to facilitate cutting. The embodiment comprises the following steps: (a) delivering electrolyte liquid to the treatment site for a controlled amount of time (and terminating delivery of fluid), (b) applying RF energy to the occlusion through electrode 19 while advancing electrosurgical device 20, (c) stopping the delivery of energy when advancement of electrosurgical device 20 has slowed or stopped (i.e. has been impeded), and (d) repeating steps (a) through (c) as needed to advance through an occlusion.

Any of the above described methods of crossing CTOs may include using a slow, continual flow of contrast fluid from the aperture as the operator advances electrosurgical device 20 such that a small trail of contrast fluid is left in the channel, thereby creating visible trace of the pathway of electrosurgical device 20.

Figure 15A:
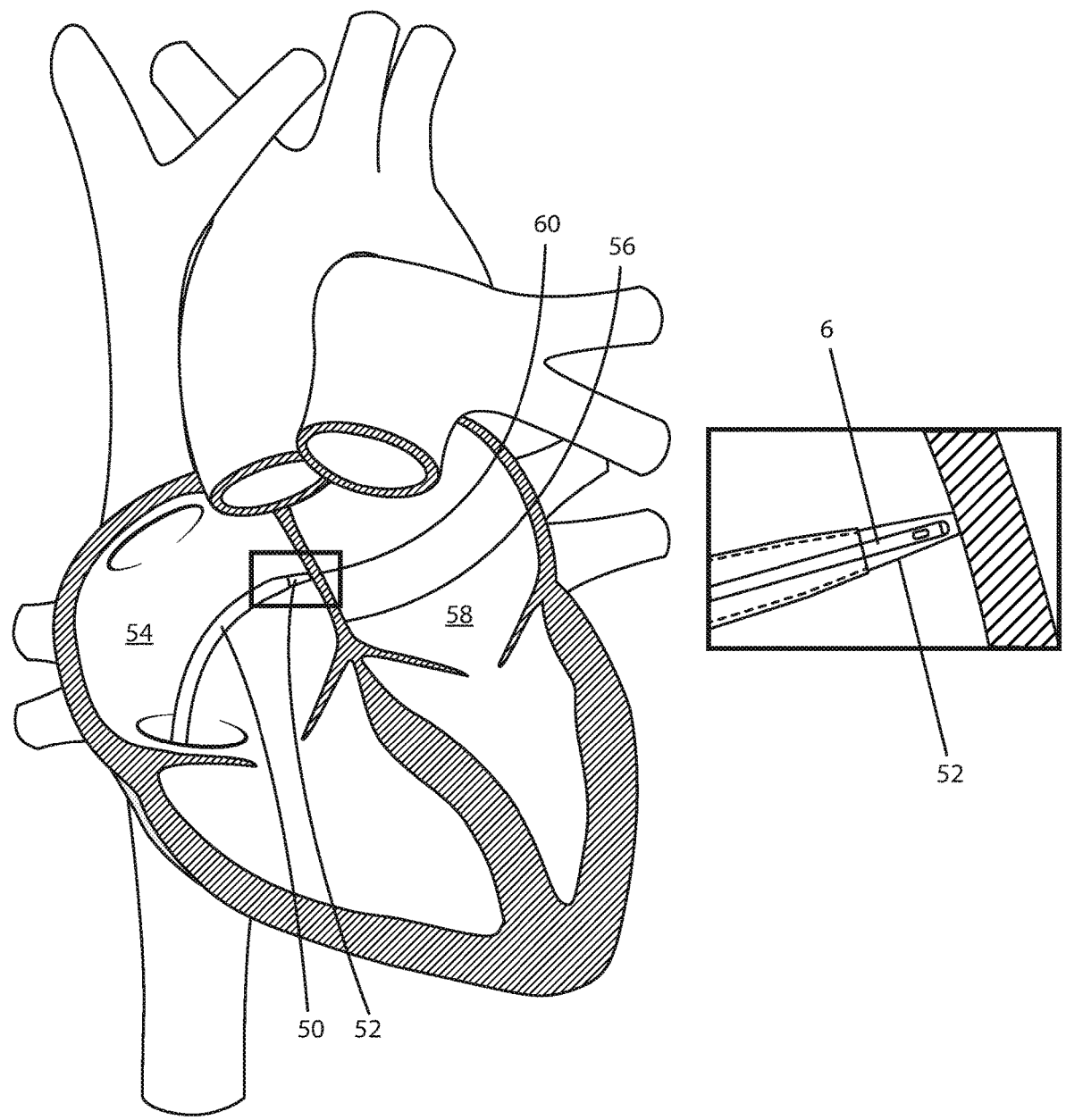
FIGS. 15A and 15B illustrate the steps of an embodiment of a method used in a transseptal procedure.
Figure 15B:
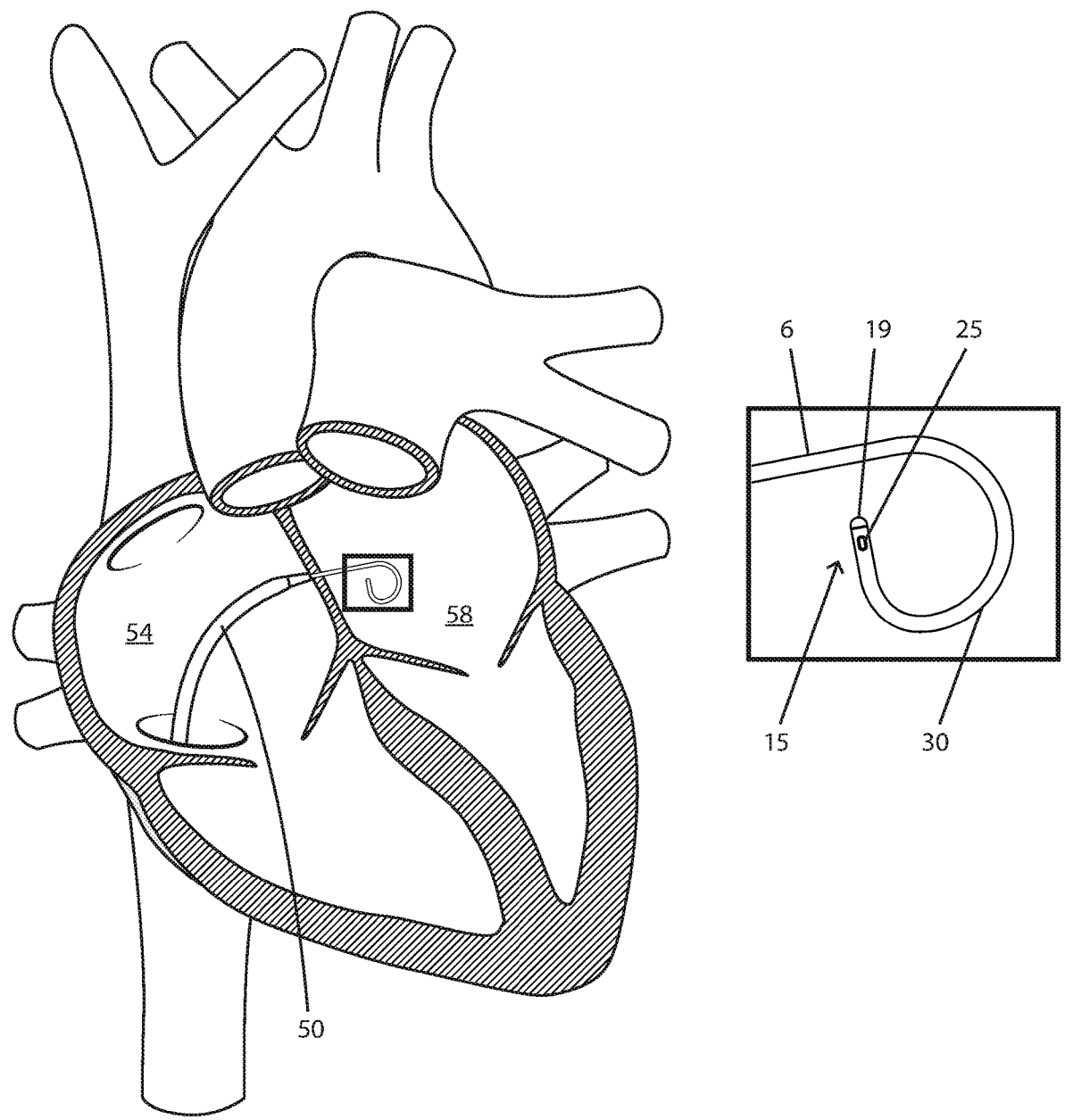

A further aspect of the invention is a method of creating a transseptal puncture. With reference now to FIGS. 15A and 15B, an embodiment of this method aspect may comprise the following steps (i) introducing an electrosurgical device 20 into a body of a patient, the electrosurgical device 20 comprising an elongate member 6 having a distal region 24 and a proximal region 22, an energy delivery device 15 proximate to the distal region capable of cutting material, and a lumen 26 and apertures 25 operable to communicate with a pressure sensing mechanism (not shown) for determining pressure in the body proximate to the distal region 24; (ii) positioning the energy delivery device 15 at a first desired location in the patient's body adjacent material to be cut; (iii) delivering energy using the energy delivery device 15 to cut the material; and (iv) measuring pressure in the body using the pressure sensing mechanism in order to determine the position of the electrosurgical device 20 before and/or after step (iii). In some embodiments of this aspect, step (ii) comprises delivering fluid, such as contrast fluid, for imaging at the first desired location in the patient's body.

Some embodiments of the method further comprise step (v) advancing the device to a second desired location. In certain embodiments of this aspect, the medical device comprises at least one radiopaque marker 5 and step (v) comprises monitoring at least one of the radiopaque markers 5. Some embodiments of the method comprise step (vi) measuring pressure at the second location. The medical device may comprise at least one radiopaque marker 5 and step (vi) may be performed after confirming the position of the pressure sensing mechanism at the second location using the radiopaque markers.

For some embodiments, step (i) comprises introducing the device into the patient's vasculature (and/or other body lumens). The step of introducing the device into the patient's vasculature may comprise inserting the device 20 into a dilator 52 and a guiding sheath 50 positioned in the patient's vasculature. In certain embodiments, the device 20 and at least one of the dilator 52 and sheath 50 each comprise a radiopaque marking, and step (ii) comprises aligning the radiopaque markings to aid in positioning the device. For certain alternative embodiments of the method, step (v) comprises advancing the dilator 52 and the sheath 50 into the second location together over the spatially fixed electrosurgical device 20. In other alternative embodiments, step (v) comprises advancing the dilator, sheath, and medical device all together into the second location.

In certain embodiments of this method aspect, the material to be cut is tissue located on an atrial septum 56 of a heart. Further, the region of tissue may be the fossa ovalis 60 of a heart. In such a case, the pressure measured at the first location is the blood pressure in the right atrium 54, and the pressure measured at the second location is the blood pressure in the left atrium 58.

In some alternative embodiments, the method further includes delivering imaging fluid that is visible using an imaging system in order to confirm the position of the electrosurgical device 20 at the second desired location.

In certain embodiments of the method, the medical device, dilator, and sheath are introduced into the heart via the inferior vena cava (as shown in FIGS. 15A and 15B). In alternative embodiments, the heart is accessed from the superior vena cava. Further details regarding superior and inferior approaches to the heart may be found in U.S. patent application Ser. No. 13/113,326 (filed on May 23, 2011), and Ser. No. 11/265,304 (filed on Nov. 3, 2005) both of which are incorporated in their entirety herein by reference.

Thus, as described herein above, embodiments of the present invention include an electrosurgical device comprising an electrically conductive elongate member for traversing body vasculature configured and operable to allow energy to flow through the wall of the elongate member; a hollow lumen defined by the elongate member with one or more apertures defined by a wall of the elongate member at or near its distal end; and an energy delivery device in electrical communication with the elongate member located at or about the distal end of the member. The energy delivery device has an electrode for delivering energy and a thermal shield is positioned between the electrode and the elongate member for protecting portions of the device from heat associated with the delivery of energy to tissue via the electrode. Method aspects of the present invention include using the electrosurgical device to traverse body vasculature of a patient and to deliver both fluid and electrical energy from or about its distal end.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. An electrosurgical device comprising:
an elongate member which is flexible and tubular defining an electrically conductive sidewall for delivering electrical energy therethrough, the electrosurgical device defining a lumen that is in fluid communication with a distal aperture;

an energy delivery device including an electrode at a distal tip of the electrosurgical device, the electrode being distal to and spaced apart from the elongate member, the electrode being a first piece of metal and the elongate member being a second piece of metal wherein the first piece of metal and the second piece of metal are separate pieces of metal and not in contact with each other, and the electrode being in electrical communication with the electrically conductive sidewall of the elongate member by means of an support spine which is electrically conductive;

the energy delivery device and the elongate member being connected by an insulation layer which has a tubular configuration; and the support spine being flexible and electrically conductive, and extending proximally from the energy delivery device within a distal portion of the lumen with a proximal end of the support spine being located within the distal portion of the lumen, wherein a proximal end of the support spine is not coupled to the elongate member whereby the proximal end of the support spine is able to move laterally relative to the electrically conductive sidewall of the elongate member such that the proximal end of the support spine can contact the electrically conductive sidewall such that the energy delivery device is in electrical communication with the electrically conductive sidewall of the elongate member via the support spine.

2. The electrosurgical device of claim 1, wherein the insulation layer covers the elongate member.

3. The electrosurgical device of claim 1, wherein the insulation layer is flexible.

4. The electrosurgical device of claim 1, wherein the insulation layer is rigid.

5. The electrosurgical device of claim 1, wherein the energy delivery device comprises an electrically conductive spacer, the electrically conductive spacer being in electrical communication with and connected to the electrode.

6. The electrosurgical device of claim 1, wherein a proximal portion of the support spine includes a bent portion to facilitate contact with the electrically conductive sidewall of the elongate member.

* * * * *